Figure 1:
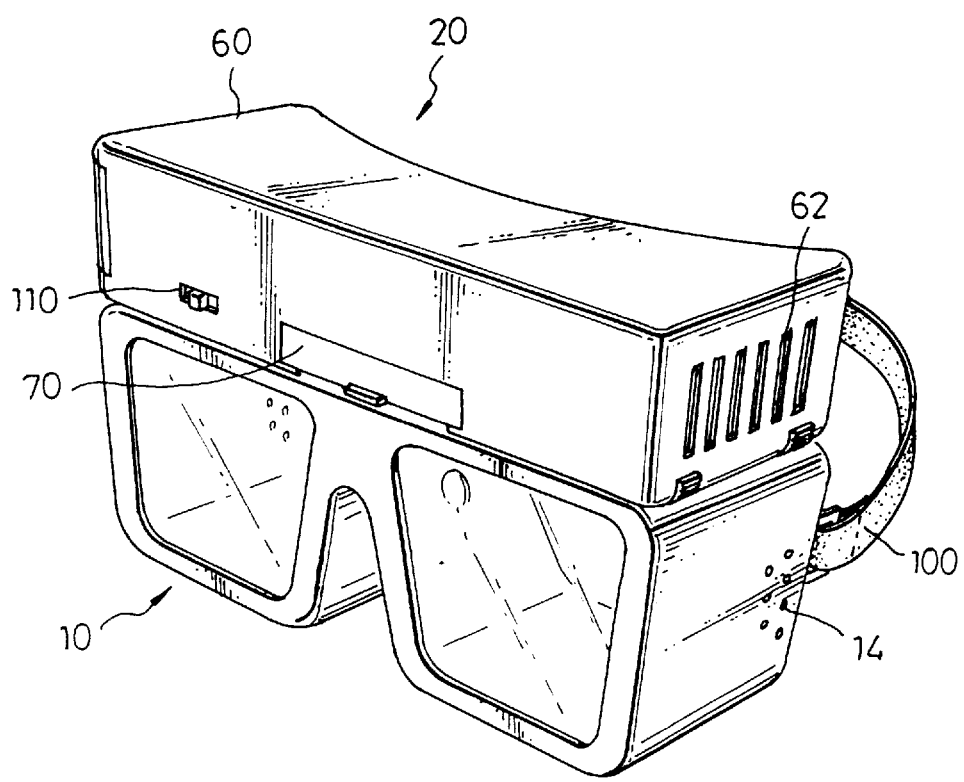
Figure 2:
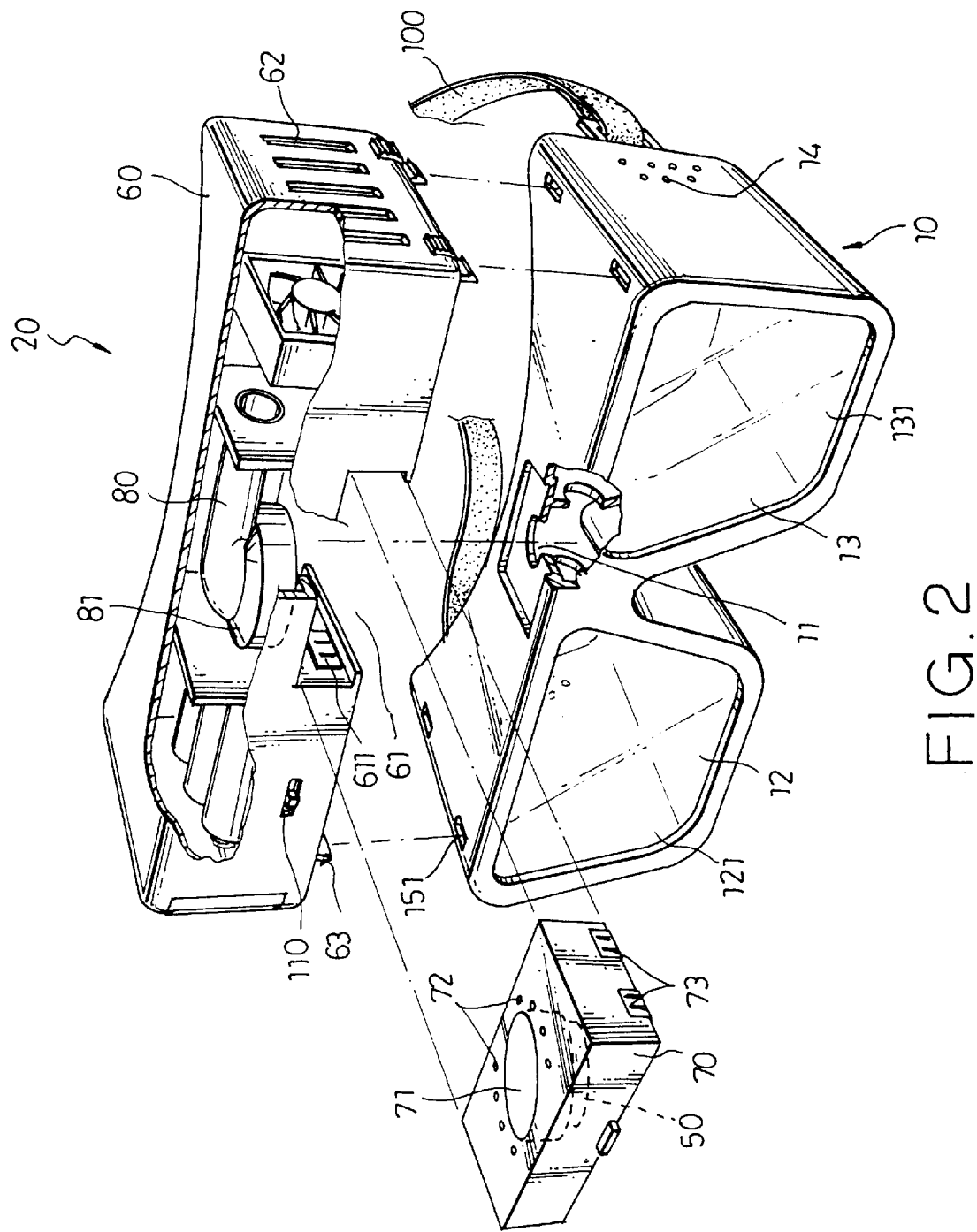
Figure 3:
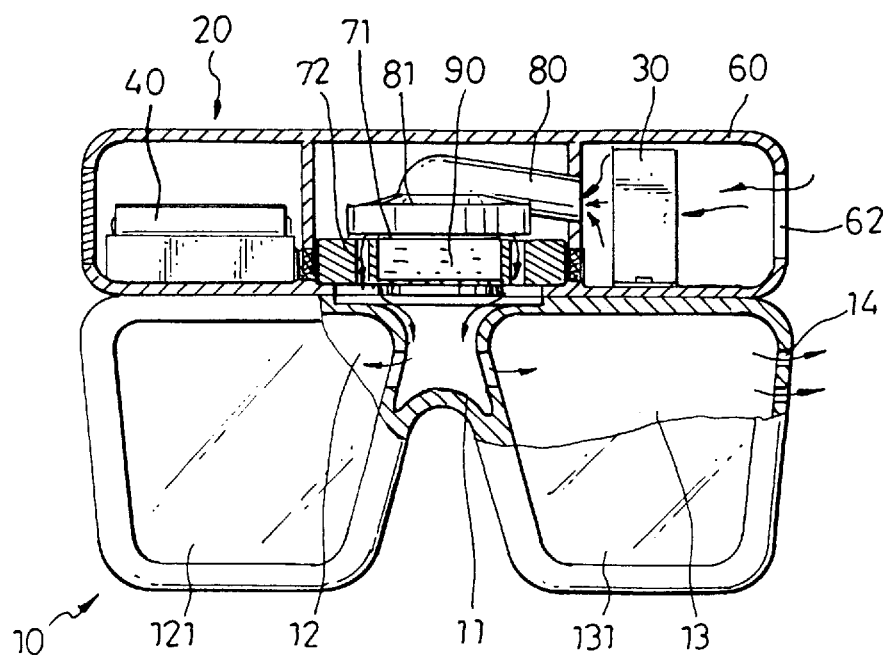

United States Patent [19]
Kang

[11] Patent Number: 5,807,357
[45] Date of Patent: Sep. 15, 1998

[54] COMPACT NEBULIZER FOR TREATING THE EYES

[76] Inventor: Meng-Che Kang, 3F, No. 25, Lane 283, Tun Hua N. Rd., Taipei, Taiwan

[21] Appl. No.: 914,157

[22] Filed: Aug. 19, 1997

[51] Int. Cl.⁶ .................................................. A61M 35/00
[52] U.S. Cl. ........................... 604/294; 604/296; 604/297
[58] Field of Search ................................ 604/20, 22, 289, 604/294, 296, 298, 300, 297; 2/6.3, 426

[56] References Cited

U.S. PATENT DOCUMENTS

| | | | |
|---|---|---|---|
| 4,193,401 | 3/1980 | Marinello | 604/294 |
| 4,573,982 | 3/1986 | Forbes et al. | 604/300 |
| 4,952,212 | 8/1990 | Booth et al. | |
| 5,053,000 | 10/1991 | Booth et al. | |
| 5,171,306 | 12/1992 | Vo | 604/298 |
| 5,368,582 | 11/1994 | Bertera | 604/294 |
| 5,630,793 | 5/1997 | Rowe | 604/294 |

Primary Examiner—John G. Weiss
Assistant Examiner—David J. Cho
Attorney, Agent, or Firm—Bacon & Thomas

[57] ABSTRACT

A compact nebulizer for treating the eyes, including a goggles unit having an air hole and at least one air chamber communicating with the air hole and fitting over the user's eyes, and a nebulizer unit detachably attached to the goggles unit, the nebulizer unit having a housing holding a power supply device, an electric fan and a nebulizer, the housing having at least one air intake hole and at least one air outlet hole disposed in communication with the air hole of the goggles unit.

3 Claims, 3 Drawing Sheets

COMPACT NEBULIZER FOR TREATING THE EYES

BACKGROUND OF THE INVENTION

The present invention relates to a nebulizer, and more specifically to a compact nebulizer for treating the eyes.

Various ocular treatment methods and apparatus have been disclosed for treating the eyes. Examples of such are seen in U.S. Pat. No. 4,952,212 entitled "OCULAR TREATMENT" and U.S. Pat. No. 5,053,000, entitled "OCULAR TREATMENT". However, these conventional ocular treatment devices are neither compact nor convenient for personal use.

SUMMARY OF THE INVENTION

It is one object of the present invention to provide a compact nebulizer which is designed to reduce an eye treatment solution to a fine spray for treating the eyes or the surrounding areas of the eyes. It is another object of the present invention to provide a compact nebulizer for treating the eyes which is suitable for personal use. It is still another object of the present invention to provide a compact nebulizer which is detachable, and convenient for sterilization. According to the present invention, the compact nebulizer comprises a goggles unit and a nebulizer unit detachably attached to the goggles unit. The goggles unit fits snugly against the face over the eyes. The nebulizer unit comprises a housing having at least one air intake hole and at least one air outlet hole, a power supply device mounted inside the housing, an electric fan mounted inside the housing and connected to the power supply device and controlled to draw currents of air from outside through the at least one air intake hole of the housing into the air hole of the goggles unit and the at least one air chamber, and an ultrasonic oscillator mounted inside the housing and connected to the power supply device and controlled to reduce an eye treatment solution to a fine spray, permitting it to be carried by with currents of air into the at least one air chamber.

BRIEF DESCRIPTION OF THE DRAWINGS

FIG. 1 is a perspective view of a compact nebulizer for treating the eyes according to the present invention;

FIG. 2 is an exploded perspective view of the compact nebulizer shown in FIG. 1; and FIG. 3 is a partial sectional view of the compact nebulizer shown in FIG. 1.

DETAILED DESCRIPTION OF THE PREFERRED EMBODIMENT

Referring to FIGS. 1 and 2, a compact nebulizer in accordance with the present invention is generally comprised of a goggles unit 10, and a nebulizer unit 20. The goggles unit 10 comprises an air hole 11 in the middle, a left air chamber 12, a right air chamber 13, and a plurality of mounting holes 151 bilaterally disposed at its top. The air hole 11 communicates with the left air chamber 12 and the right air chamber 13. The nebulizer unit 20 is comprised of an electric fan 30, a power supply device (battery set) 40, an ultrasonic oscillator 50, and a housing 60. The housing 60 has a bottom chamber 61 in the middle, and a plurality of mounting rods 63 bilaterally raised from its bottom side. A sliding box 70 is inserted into the bottom chamber 61. The sliding box 70 comprises a basin 71. The ultrasonic oscillator 50 is fastened to the bottom side of the basin 71 of the sliding box 70. The electric fan 30 and the power supply device 40 are respectively mounted inside the housing 60 at two opposite ends. The housing 60 has a plurality of air intake holes 62 at one end through which currents of air are drawn into the housing 60 by the electric fan 30. The sliding box 70 has a plurality of air outlet holes 72 spaced around the basin 71. An air duct 80 is mounted inside the housing 80 adjacent the electric fan 30, having a hood 81 at one end remote from the electric fan 30 and covered o the air outlet holes 72 of the sliding box 70.

Referring to FIGS. 2 and 3 again, when an eye treatment solution 90 is poured in the basin 71, the sliding box 70 is inserted into the bottom chamber 61 of the housing 60, then the mounting rods 63 of the nebulizer unit 20 are respectively plugged into the mounting holes 151 of the goggles unit 10. Further, the goggles unit 10 is equipped with a strap 100 adapted for fastening to the user's head. The sliding box 70 has metal contacts 73 disposed on the outside and connected to the ultrasonic oscillator 50 by conductors. The housing 60 has metal contacts 611 inside the bottom chamber 61, and connected to the two opposite terminals of the power supply device 40 by conductors. An On/Off switch 110 is mounted on the housing 60 to control the operation of the electric fan 30 and the ultrasonic oscillator 50. When the sliding box 70 is inserted into the bottom chamber 61 of the housing 60, the metal contacts 73 of the sliding box 70 are respectively forced into contact with the metal contacts 611 of the housing 60. When the On/Off switch 110 is switched on, the power supply device 40 is electrically connected to the electric fan 30 and the ultrasonic oscillator 50. When the electric fan 30 and the ultrasonic oscillator 50 are started, the eye treatment solution 90 is oscillated by the ultrasonic oscillator 50 and reduced to a fine spray, and the fine spray of eye treatment solution 90 is then carried by currents of air induced by the electric fan 30 through the air hole 11 into the left air chamber 12 and the right air chamber 13 to treat the eyes.

Referring to FIGS. 1 to 3 again, the left air chamber 12 and the right air chamber 13 are covered with a respective transparent glass 121;131. A plurality of exhausting holes 14 are made at the goggle unit 10 for exhaust air. Air filter means may be installed in the air intake holes 62 to remove dust from intake air.

While only one embodiment of the present invention has been shown and described, it will be understood that various modifications and changes could be made thereunto without departing from the spirit and scope of the invention disclosed.

What the invention claimed is:

1. A compact nebulizer for treating the eyes, the nebulizer comprising:

a) a goggles unit for fitting over the eyes of a user, the goggles unit including an air hole and at least one air chamber for receiving the eyes of the user;

b) a nebulizer unit detachably attached to the goggles unit, the nebulizer unit including a housing having at least one air intake hole and at least one air outlet hole, a power supply device mounted inside the housing, an electric fan mounted inside the housing and connected to the power supply device and controllable to draw currents of air from the outside through the at least one air intake hole of the housing and into the air hole of the goggles unit and the at least one air chamber; and c) the housing further including a sliding chamber, an ultrasonic oscillator mounted in a sliding box that is inserted into the sliding chamber, the sliding box including a basin for holding an eye treatment solution, a plurality of air outlet holes spaced around the basin, the ultrasonic oscillator being connected to the power supply device and controllable for reducing the eye treatment solution to a fine spray and permitting the fine spray to be carried with currents of air into the at least one air chamber.

2. The compact nebulizer of claim 1, wherein said goggles unit comprises an air duct having one end facing said electric fan and adapted for receiving currents of air from it and an opposite end mounted with a hood covered over the air outlet holes and basin of said sliding box.

3. The compact nebulizer of claim 1, wherein said goggles unit has a plurality of mounting holes at a top side thereof, said housing of said nebulizer has a plurality of downward mounting rods respectively fastened to the mounting holes of said goggles unit.

* * * * *